United States Patent [19]

Melcher et al.

[11] 4,137,991
[45] Feb. 6, 1979

[54] CLAMPED ACOUSTIC ELASTIC WAVE GENERATOR

[75] Inventors: Robert L. Melcher, Yorktown Heights; Robert J. von Gutfeld, New York, both of N.Y.

[73] Assignee: International Business Machines Corporation, Armonk, N.Y.

[21] Appl. No.: 744,354

[22] Filed: Nov. 23, 1976

[51] Int. Cl.² .................... G10K 10/00; G01N 29/00
[52] U.S. Cl. ...................................... 181/142; 73/643
[58] Field of Search ............... 181/0.5, 142; 331/94.5, 331/DIG. 1; 330/5.5; 250/493; 73/67.8 S, 67.2

[56] References Cited

U.S. PATENT DOCUMENTS

| | | | |
|---|---|---|---|
| 3,322,231 | 5/1967 | Gournay | 331/DIG. 1 |
| 3,392,258 | 7/1968 | Bruma et al. | 331/DIG. 1 |
| 3,392,368 | 7/1968 | Brewer et al. | 181/0.5 |
| 3,532,181 | 10/1967 | DeMaria et al. | 250/493 |
| 3,583,212 | 6/1971 | Nanney et al. | 330/5.5 |

OTHER PUBLICATIONS

*Journal of the Acoustical Society of America,* vol. 49, No. 3 (Part 3), Dec. 1971, G. Cachier, "Laser Excitation of Microwave Sound in Solids", pp. 974–978.
*Journal of Applied Physics,* vol. 34, No. 12, Dec., 1963 pp. 3559–3567, R. M. White, "Generation of Elastic Waves by Transient Surface Heating".
*IBM Technical Disclosure Bulletin,* vol. 18, No. 7, Dec. 1975, R. L. Melcher et al., "Multichannel, Random Access Acoustic Echo Storage Memory".
J. C. Bushnell et al., "Thermoelastic Stress Production in Solids", *Journal of Applied Physics,* vol. 39, No. 12, pp. 5541–5546, 1968.
L. S. Gournay, "Conversion of Electromagnetic to Acoustic Energy by Surface Heating", *Journal of the Acoustical Society of America,* vol. 40, No. 6, pp. 1322–1330 (1966).
N. C. Anderholm, "Laser-Generated Stress Waves", *Applied Physics Letters,* vol. 16, No. 3, pp. 113–115 (1970).
M. P. Felix, "Distortion of Short-Duration Stress Pulses Propagating in Solids and Liquids", *Journal of the Acoustical Society of America,* vol. 58, No. 3, pp. 626–629 (1975).

*Primary Examiner*—Maynard R. Wilbur
*Assistant Examiner*—Lawrence Goodwin
*Attorney, Agent, or Firm*—Graham S. Jones, II

[57] ABSTRACT

A pulse of energy including atomic, thermal or electromagnetic radiation produced by a source such as an electron or atomic beam, laser, electrical or optical means is applied to a generator. The generator includes a body of material adapted for acoustic vibration. An energy absorbing layer is in intimate acoustic contact with the body of material so that acoustic vibrations generated in the absorbing layer are transmitted to the body of material. The surface of the absorbing layer opposite to the body of material is acoustically clamped in position by a solid clamping medium.

17 Claims, 12 Drawing Figures

CLAMPED ACOUSTIC ELASTIC WAVE GENERATOR

BACKGROUND OF THE INVENTION

1. Field of the Invention

This invention relates to generation of acoustic waves and more particularly to devices for enhancing the efficiency of propagation of acoustic waves by an energy-acoustic transducer utilizing the principle of thermoelastic expansion.

2. Description of the Prior Art

U.S Pat. No. 3,532,181 of De Maria et al. entitled "Laser Induced Acoustic Generator" teaches directing a pulse train from a laser onto a thin absorbing film which is preferably bonded or deposited on an acoustic transmitting medium such as a crystalline bar. The film may be sandwiched between two crystals. A single crystal material is preferred, and use of a liquid cell is mentioned. The thin film is preferably of Au, SN, Cu or Ag. No mention is made of the fact that it is desirable to clamp the film acoustically to enhance the performance of the device.

"Generation of Elastic Waves by Transient Surface Heating" by R. M. White, Journal of Applied Physics, Vol. 34, No. 12, December 1963, pp. 3559–3567 teaches at p. 3563 the theoretical concept of constraining the surface of the energy absorbing material which is discussed mathematically. A special case is described corresponding to a "constrained surface in which two identical semi-infinite bodies meet at a plane where they are welded together and where energy absorption takes place . . . . This mathematical model may be used to simulate the absorption of r.f. energy at the joint between two transparent media which are slightly absorptive near their common boundary." There is no suggestion of any practical way in which any amplitude enhancement can be achieved by constraining the boundary of the energy absorbing layer. Hence, this reference teaches no method of using the effect.

"Laser Excitation of Microwave Sound in Solids" by Cachier, Journal of the Acoustical Society of America, Vol. 49, No. 3 (Part 3), pp. 974–978 shows on page 977 a titanium layer of 500 Angstroms thickness which is absorptive of all light deposited over a gold film of 1 micron thickness which in turn is deposited upon a 1000 Angstroms thick titanium film deposited upon a crystal delay line. The first layer of titanium is a laser energy absorbing layer, and it is exposed to the atmosphere without any constraint.

U.S. Pat. No. 3,322,231 of Gournay shows a laser source aimed through a glass window in a clamping plate into a liquid (water) to generate seismic pulses. In this case, no intermediate absorptive layer is employed to convert light energy to acoustic energy. Furthermore, no highly absorptive material is employed because water is only slightly absorptive of the light being used. Instead, the transparent body of water itself is required to absorb the energy. The glass and the plate which can be quite extensive are employed to provide a clamp of the upper surface of the fluid. The use of concentrated electromagnetic energy is required to provide high output. Even any highly pigmented liquid would not produce high absorption as it would have a relatively large optical absorption length yielding a small optical energy absorption. "Multichannel, Random-Access Acoustic Echo Storage Memory" by Melcher et al., the inventors hereof, in the IBM Technical Disclosure Bulletin, Vol. 18, No. 7, December 1975, pp. 2362–3, teaches provision of a block of solid material coated with laser energy absorbing thin film segments which are coated with a transparent overlay to shorten thermal relaxation times.

All of the above prior art shows that while many of the elements of the instant invention have been available in the prior art, they have not been combined heretofore to provide the improved results which are achieved by employing the present invention.

SUMMARY OF THE INVENTION

An object of this invention is to provide a transducer which converts energy into an acoustic form and which has a high degree of efficiency.

Another object of this invention is to provide a transducer of energy into acoustic form which retains the energy converted efficiently within the medium to which it is transferred for delivery to the output of such medium.

Still another object of this invention is to generate localized and/or scannable well collimated acoustic energy which can be utilized in such applications as non-destructive flaw detection.

In accordance with the invention, apparatus is provided for generating acoustic waves in response to application of a source of energy. A body of material adapted for acoustic vibration is in intimate acoustic contact with an energy absorbing layer composed of a material adapted for absorbing a predetermined form of energy. A solid clamping material is in intimate acoustic contact with said absorbing layer.

DESCRIPTION OF THE PREFEERRED EMBODIMENT

Figure 1A:
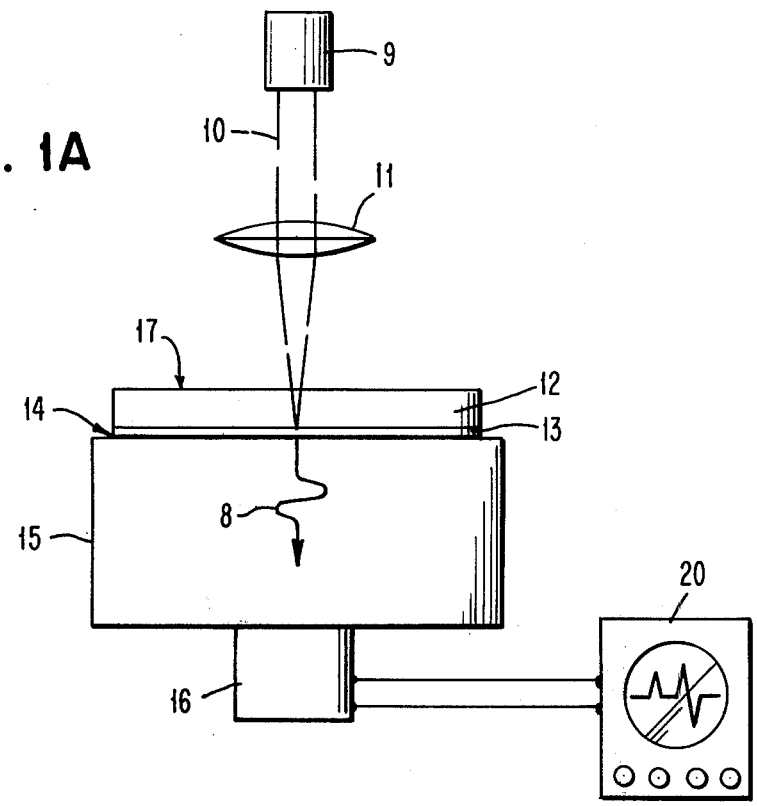
FIG. 1A shows a typical transducer structure for generating elastic, acoustic waves from a constrained boundary.

FIG. 1A shows laser 9 providing a pulsed laser beam 10 directed through lens 11 to focus upon an evaporated absorbing film 13 of tungsten or molybdenum about 2000Å thick deposited upon the lower surface of a dielectric thin plate 12 of a material such as polished glass, quartz, or sapphire ($Al_2O_3$) transparent to laser beam 10. Film 13 is acoustically bonded with a preferably solid or viscous liquid bonding agent 14 such as propylene glycol, silicone oil, stopcock grease, epoxy resin, wax, or Canada Balsam to a solid sample 15 composed of a material selected from quartz, $Al_2O_3$ (sapphire), ceramics, metals, semiconductors, dielectrics, or a container of liquid. A ceramic piezoelectric transducer-receiver 16 sensitive to compressional waves such as a Panametrics, M 116 20 Mhz ± 5 Mhz can be used. Its output may be amplified and displayed either on an oscilloscope or an x-y recorder used in conjunction with the output of a boxcar integrator. In a particular experiment using the above equipment and 5 nanosecond laser pulses, incident power levels are of the order of 350W (corresponding to only $2 \times 10^{-6}$J).

In operation of this embodiment of the invention then, a pulse of laser light 10 or other optical energy is applied to solid body 15 (e.g., quartz) in intimate contact at one surface with a thin film 13 of an energy absorbing material which, when energized, causes mechanical (acoustic) waves to be generated in body 15. Absorbing layer 13 is acoustically in contact with another "clamping" medium 12 which is acoustically "clamped" to it in the sense that the mechanical vibration of the absorber layer is clamped or limited by the "clamping" medium which can be a clear fluid or a transparent solid such as quartz, $SiO_2$, etc. The ideal is for the clamping medium 12 to reflect all mechanical motion generated by absorbing layer 13 back into the absorbing layer by pressing against it at all points with a gap as a fluid can do or as a bonded solid can do if bonded sufficiently. Thus, through "clamping" film 13 is confied at that surface, and when it attempts to expand, its expansion is constrained so greater vibration of the solid body is produced, and greatly enhanced elastic wave 8 is generated and launched into the solid body 15. Transducer 16, which is sensitive to the vibration, produces an output on oscilloscope 20.

Figure 1B:
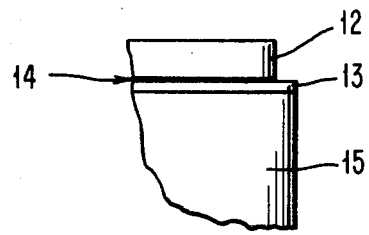
FIGS. 1B and 1C show alternative forms of the transducer of FIG. 1A.

Alternatively, film 13 can be deposited upon sample 15 and plate 12 can be bonded to film 13 by acoustic bonding agent 14 as shown in FIG. 1B.

Figure 1C:
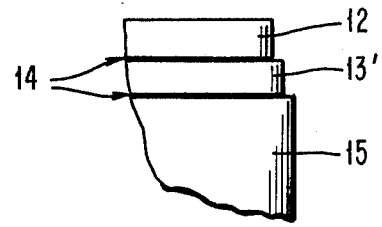

In still another embodiment shown in FIG. 1C, film 13 is replaced by a thin plate 13' of energy absorbent material which is bonded by agent 14 above to plate 12 and below to material 15.

Figure 2:
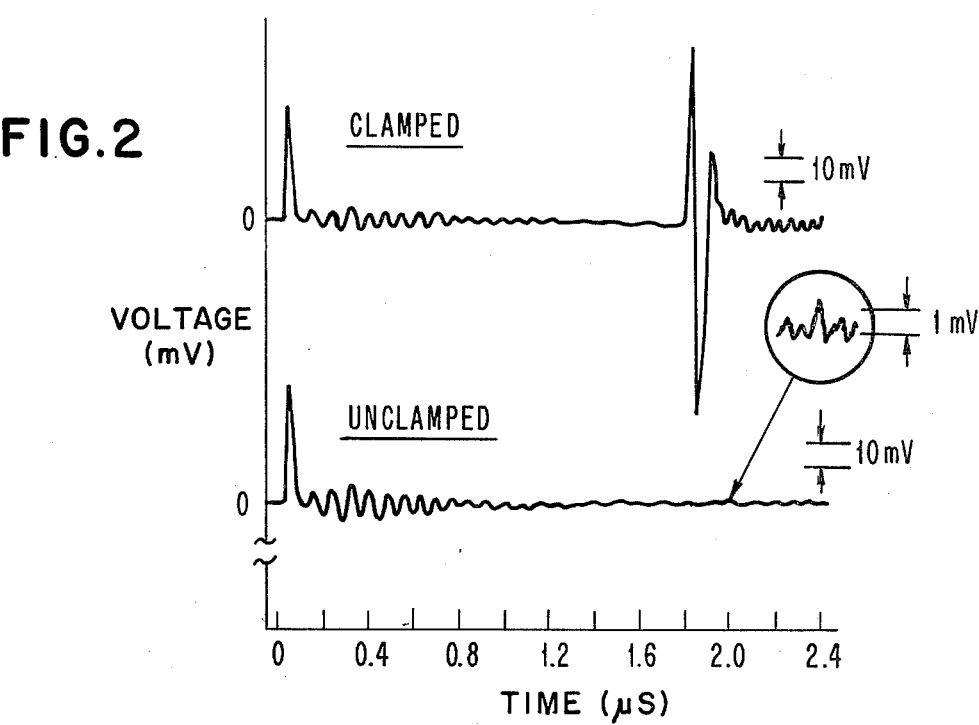
FIG. 2 shows a voltage vs. time graph of an optically detected laser pulse at $t=0$ followed by a piezoelectrically detected pulse at time $t=1.8\mu s$ for the clamped structure of FIG. 1, as well as a similar graph for an unclamped sample with the enlarged insert sample encircled at time $t=1.9\mu s$.

FIG. 2 shows the detected acoustic amplitudes for clamped operation of a device in accordance with FIG. 1A in response to a 5 nanosecond pulse laser excitation of a 2000°A thick Mo film 13 deposited upon a 0.025 cm thick plate 12 of $Al_2O_3$ bonded by propylene glycol to a 5 cm diameter, 0.95 cm thick fused quartz disc 15. For operation to produce the unclamped output in FIG. 2, plate 12 is inverted to bond the surface 17 of plate 12 to sample 15 by means of propylene glycol. The clamped device curve in FIG. 2 shows recorder traces of 20 MHz acoustic waves generated by a 5 nanosecond laser pulse (rhodamine 6G) incident on the Mo film 13. The peak at time $t = 0$ is the optically detected laser pulse which provides a reference time. The signal near $t = 1.8\mu s$ is the acoustic wave detected by transducer 16.

FIG. 2, unclamped, shows the results for the inverted Mo film 13 with the acoustic waves being generated at the free, unconstrained surface of film 13. The ratio R is obtained by comparing peak-to-peak amplitudes in FIG. 2 of the clamped-to-the-unclamped curves which in this case yields a value of R of about 95, or a 40 db increase.

When the same experiment was performed using chromium for film 13, a 46 db increase was achieved.

Using a thick plate 12 (0.16 cm), the results were similar to the results discussed above in connection with FIG. 2 since thickness is not critically determinative of results for thicknesses greater than the acoustic wavelength. Accordingly, in this case, the mechanical resonance of the constraining medium did not appear to affect the results.

Theoretical Considerations

The amplitude enhancement observved here can be estimated from the solution to the one-dimensional stress-strain relationship when the thermal expansion of the absorbing layer is included as a driving term. The equations as given in White, supra, have the form, $$\sigma_{xx} = \rho v^2 \epsilon_{xx} - Ba\theta \tag{1}$$

and $$\rho \frac{\delta^2 u}{\delta t^2} = \rho v^2 \frac{\delta^2 u}{\delta x^2} - Ba \frac{\delta \theta}{\delta x}. \tag{2}$$

here, $\sigma_{xx}$ is the x component of the stress tensor, $\epsilon_{xx}$, the corresponding strain, $\rho$, the density, B, the bulk modulus, $\alpha$. the thermal coefficient of expansion, $\theta$, the temperature rise above ambient, $u$, the particle displacement and $v$, the compressional wave veloctiy. White supra, has solved Eq. (2) for the case of a periodic driving term, incident at the surface of a uniform sem-infinite medium. The solutions to the instant problem are complicated by both the pulse shape of the driving term as well as the multiplicity of boundaries resulting from the different media comprising the structure. Based on preliminary estimates of a more exact treatment, the ratio, R, should fall near the range of values obtained from the perfectly free and perfectly clamped cases of White, supra.

For those limits, one obtains from White $$R = \frac{v}{(2\pi Kf)^{\frac{1}{2}}} \tag{3}$$

with $K$ the thermal diffusivity of the absorbing film and $f$ the frequency of excitation. In the experiments described herein, $f$ is determined by the receiver-transducer which is tuned to 20 ± 5 MHz. The absolute amplitude of the detected elastic wave will, of course, depend in addition on the thermal parameters of the absorbing medium as well as the Fourier component of the incident pulse shape at the frequency, $f$. For Mo, Eq. (3) yields $R = 75$ compared to an experimental value of 95 (see FIG. 2) in reasonable agreement with theory under the present approximations and estimated value for K.

Flaw Detection

Figure 3:
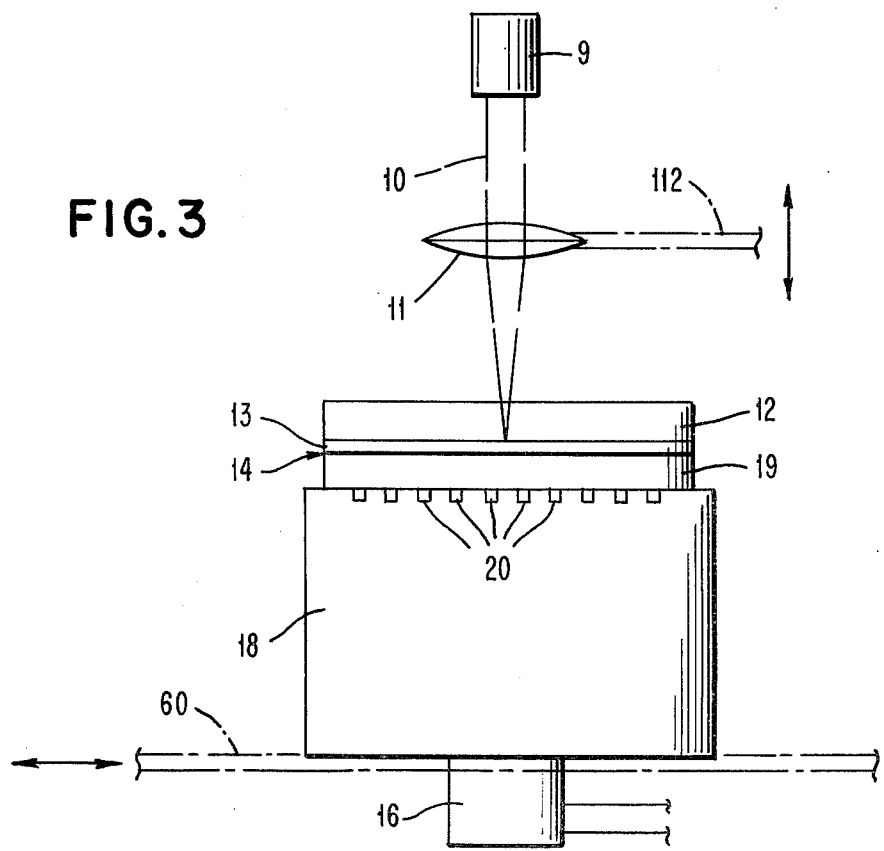
FIG. 3 shows a flaw detection application of this invention.
Figure 4:
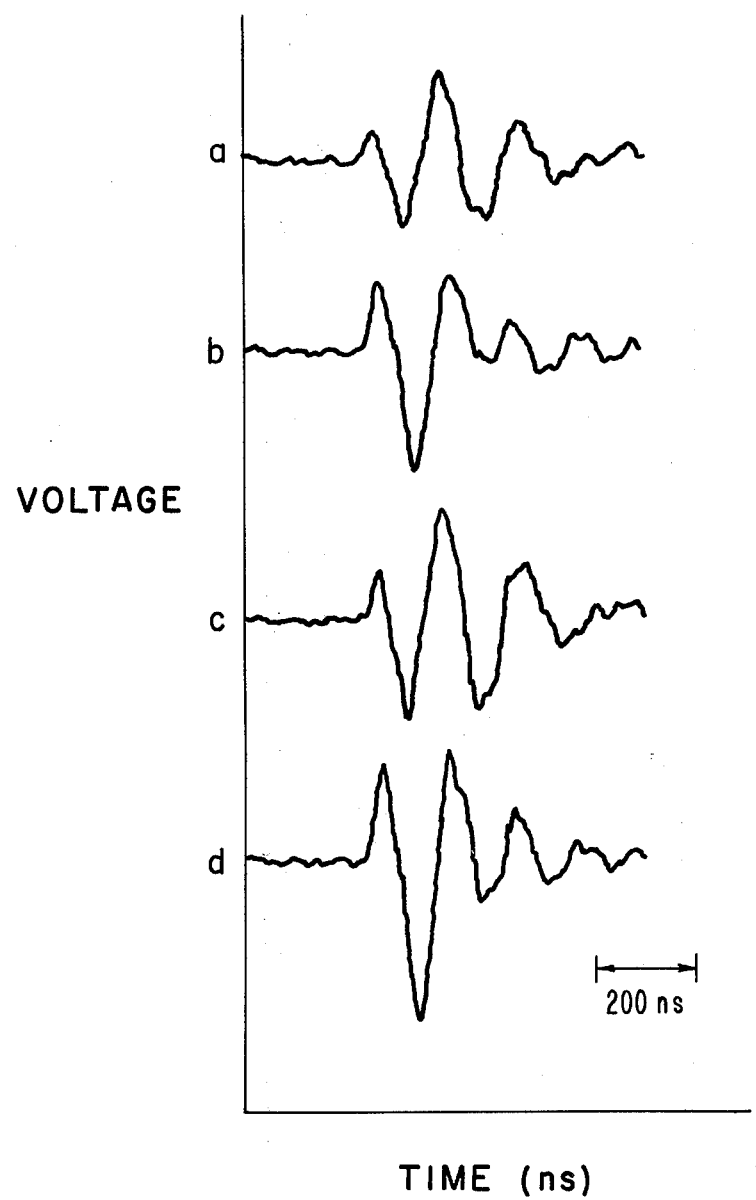
FIG. 4 shows signals illustrating output from a flaw detector designed in accordance with this invention.

Thermoelastically generated elastic waves can be employed for flaw detection in a structure designed to simulate a laminate. The structure shown in FIG. 3 consists of a 1 cm long, 1.6 cm diameter aluminum cylinder 18 with polished ends. To the top surface, a 4 mil microscope cover slide 19 is bonded to simulate a lamination. Into the top Al surface, several 0.04 cm diameter holes 20 of equal depth separated by 0.08 cm were drilled to simulate flaws at the laminate interface. Elastic waves are generated using a 10 mil $Al_2O_3$ substrate 12 and Mo film 13 combination as in FIG. 1A, with the Mo film 13 bonded to the cover slide 19. The experiment is carried out in an optical microscope with the pulsed rhodamine laser focused to approximately a 0.03 cm spot size by lens 11. Optical scanning is achieved by manual movement of the microscope stage 60 shown in phantom in FIG. 3 for transverse movement of cylinder 18 as is well known in the art. In this manner, elastic waves can be generated anywhere along the top surface of the sample and detected at the opposite surface by the Panametrics transducer 16 (active diameter, ⅛ inch). The detected patterns are shown in FIG. 4 by curves 9-d for regions corresponding to optical absorption directly above and in between the defects. Curves $a$ and $c$ show results for scanning over adjacent holes. Curves $b$ and $d$ apply to scanning spaces between holes. Note, for example, that the maximum excursion from the baseline in curves $a$ and $c$ is positive while negative in curves $b$ and $d$. The flaws at the laminate interface are distinctly visible in the transmitted acoustic pulse without the use of any additional signal processing. Flaw detection using optically generated elastic waves is achieved through this rather simple example. The scannability feature should make the present scheme particularly attractive for evaluation of samples, permitting a single receiver to be bonded at the back surface for the detection of acoustic waves generated anywhere on the front surface. Note that by simply changing the focal size of the laser spot on the absorbing medium, the diameter of the acoustic source can be changed. For example, lens 11 in FIG. 3 can be adjusted vertically by mechanical linkage 112 shown in phatom as is well known in the art. In this way, the acoustic beam can be readily changed from a plane wave ($\lambda/d << 1$) to a spherical wave ($\lambda/d >> 1$) depending on the requirements of the application, where $\lambda$ is the acoustic wavelength and d the diameter of the acoustic source. This can produce a very narrow collimated beam when $\lambda/c$ is on the order of 1. The beam can be scanned by moving the substrate beneath the beam as above or by scanning the beam across the substrate as is well known in many optical scanning systems.

Tungsten Absorber Layer

Figure 5:
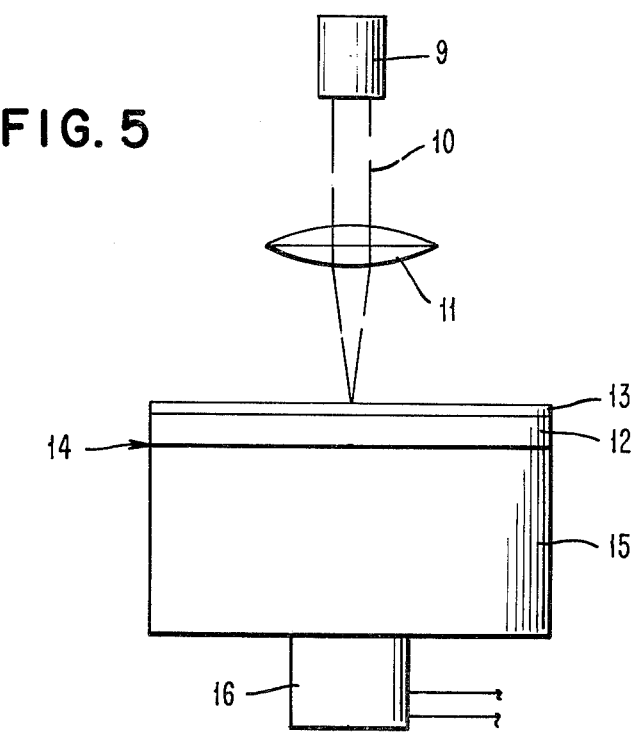
FIG. 5 shows an unclamped absorbing layer system.

Other examples of apparatus tested in connection herewith include use of an unclamped tungsten absorber layer 13 on plate 12 which is bonded to material 15. Here again, acoustic waves were generated using 5 nanosecond pulses of rhodamine 6G laser light incident upon a quartz substrate 15, first, as shown in FIG. 5. The resulting acoustic amplitude is measured by a receiver centered at 20 MHz.

In another case based upon FIG. 1A, a quartz cylinder 15 is mechanically contacted to a tungsten film 13 by means of propylene glycol 14 as an acoustic bond. The ratio of voltages measured is 1:240 corresponding to a power ratio of improvement for the clamped case of 48 db.

Aluminum on Mylar Polyester

Aluminum films 13 have been deposited onto Mylar polyester plates 12 with the plate acting as the free surface in FIG. 1A. The Al film 13 is bonded to a quartz sample 15, and a 200 times greater signal is observed compared to the FIG. 5 arrangement with the Al acting as a free surface with a Mylar polyester, propylene glycol to quartz bond.

Clamping Materials

Clamping materials for optical excitation include transparent or semi-transparent solid films or plates composed of $SiO_2$, perylene, SiO used as overlay on the energy absorbing surface. Clamping materials for electrical excitation include any of the above as well as opaque materials which are of high electrical resistivity, semi-conductive plates or overlays such as Ge, ceramics, etc.

Intrinsic Absorbing Body

Figure 6:
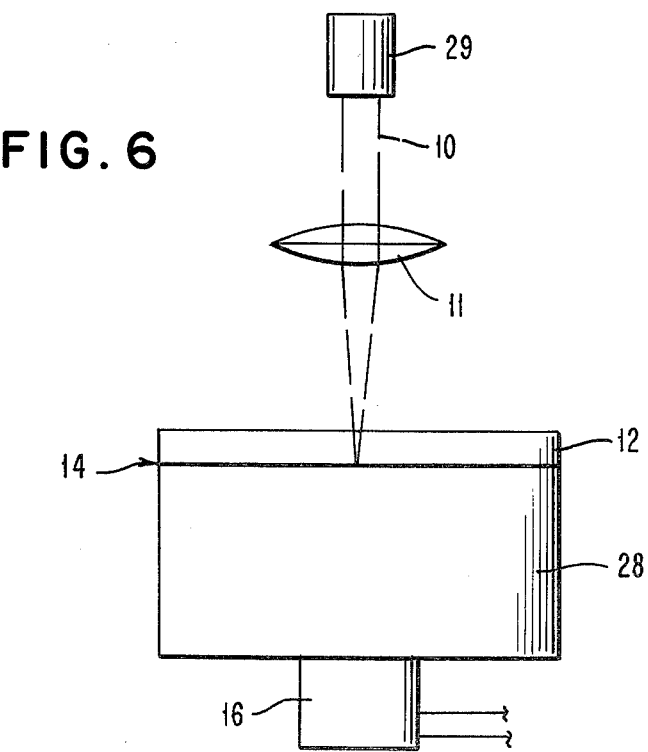
FIG. 6 shows an intrinsic absorbing material as a sample which is clamped directly without an intermediate film.

In FIG. 6, a system is shown in which a sample 28 is composed of a highly energy absorbing material. If source 29 is a visible laser, then sample 28 is composed typically of aluminum, molybdenum, tungsten, silicon, or germanium. Sample 28 is clamped directly by plate 12 through bond 14. The energy is absorbed at the highly absorbent surface of body 28.

Elastic Waves

The frequency of the elastic waves obtained in any system in accordance with this invention will be determined predominantly by the Fourier transform of the light pulse and the detailed optical and thermal parameters of all of the media comprising the structure. The optical properties apply in an optical system to the clamping and absorbing material and the thermal and elastic properties of all of the media are involved. In an electrical system the optical properties are not involved.

Figure 7:
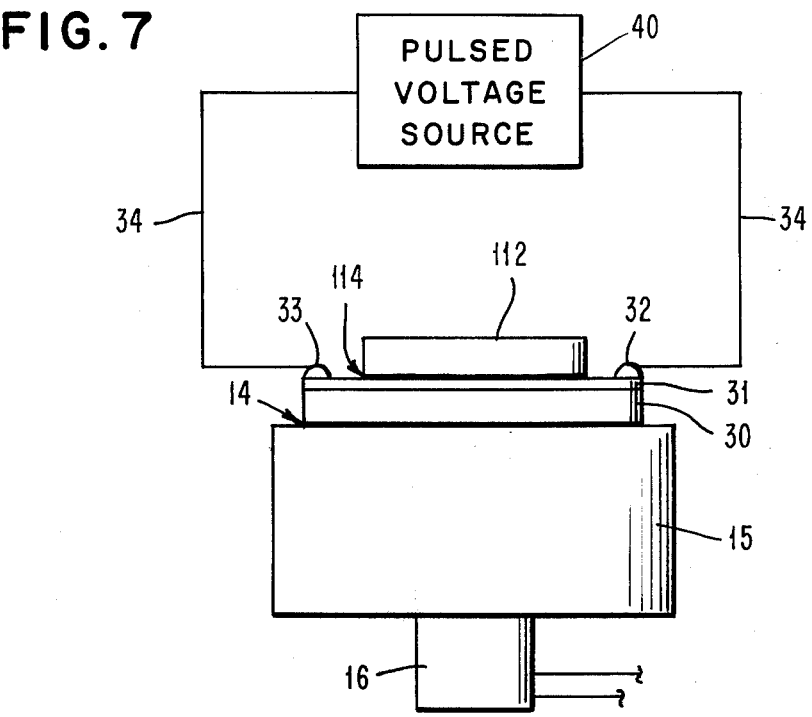
FIG. 7 shows an electrical-to-acoustic embodiment of a clamped transducer showing how electrical energy can generate acoustic waves.

FIG. 7 shows a transducer excited by electrical energy rather than optical energy. A block of material 15 has the usual piezoelectric transducer 16 attached to it. A block 30 composed of a material such as fused quartz rests upon a layer of a film of a bonding agent 14 which acoustically bonds block 30 to block 15. A thin film 31 of an electrically resistant material is coated upon block 30. Electrical leads 34 and film 31 are connected together at beads 32 and 33. A clamping block 112 is acoustically bonded by a film bonding agent 114 to film 31. When a substantial current pulse passes through film 31, the thermal energy produced launches an acoustic wave through thermoelastic expansion as explained above in connection with the systems described above. A film of 2000Å of Mo can be used for film 31 and a voltage of about 100 volts can be employed to produce about 200 watts in a 50 ohm device.

Figure 8:
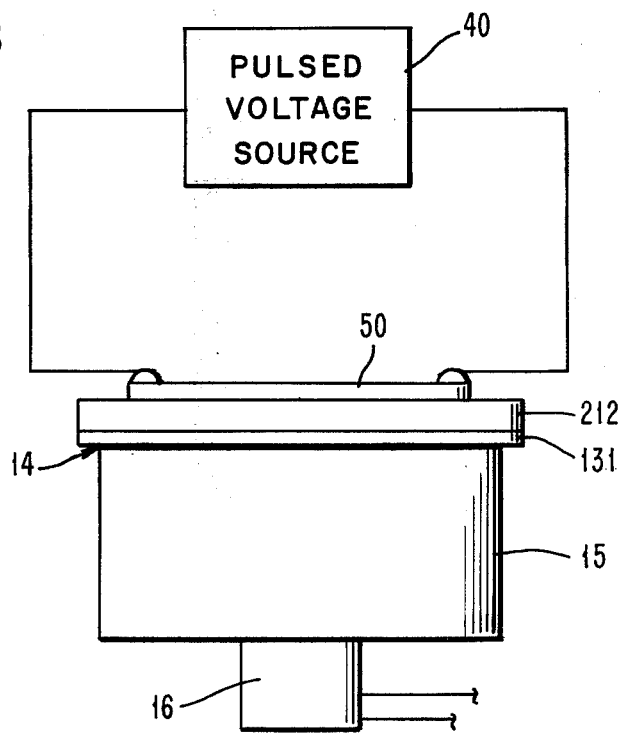
FIG. 8 shows an electrical-to-thermal-to-acoustic energy embodiment of this invention, showing how thermal energy pulses can generate acoustic waves with a clamped transducer.

FIG. 8 shows a thermal energy-to-acoustic transducer. A pulse generator supplies electrical current to a thin film strip of a conductor 50 which can be about 2000Å thick and composed of molybdenum. A plate 212 is composed preferably of single crystal $Al_2O_3$ 0.05 cm thick and serves as a clamp for another thin film strip 131 of 2000Å thick Mo on its lower surface which is adapted to be heated by heat waves transmitted through plate 212 from strip 50 to strip 131. Strip 131 is acoustically clamped by plate 212 to material 15 bonded by agent 14. Thus, strip 131 launches acoustic waves into material 15. This system should be operated at low temperatures on the order of liquid helium where streaming of thermal elastic waves produces the heating effect detected.

Figure 9:
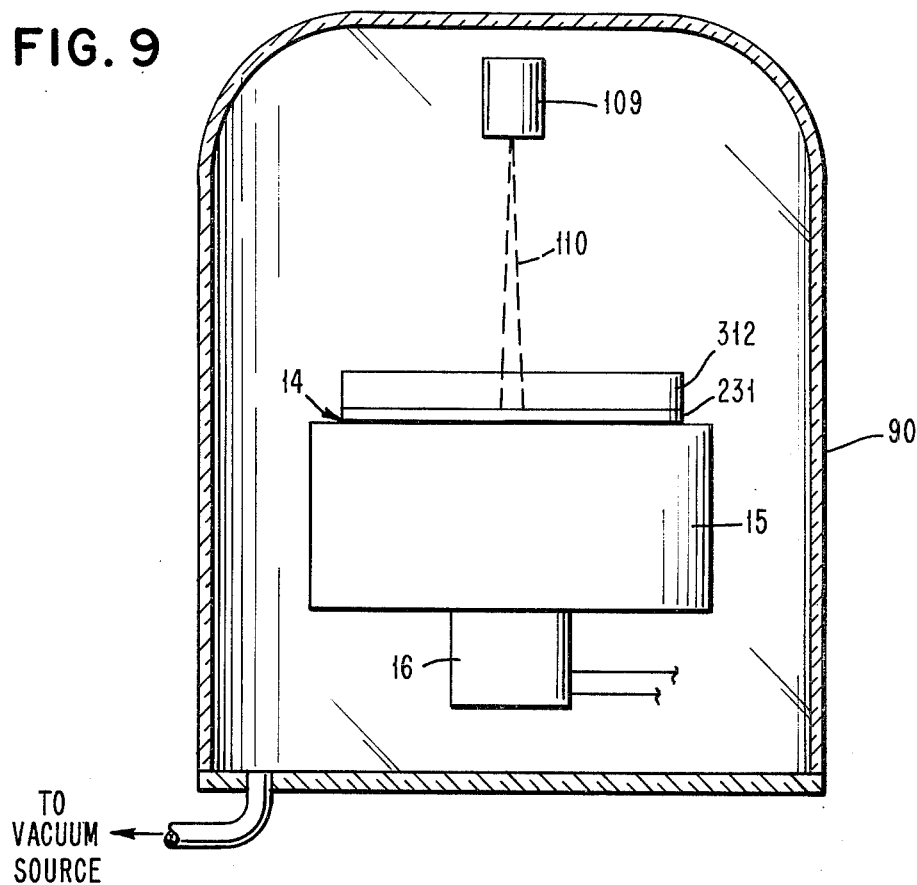
FIG. 9 shows an ion-beam-to-acoustic-energy converter.

FIG. 9 shows a source of a pulsed helium ion beam 109 in an evacuated chamber 90. A beam of helium ions 110 is directed through carbon clamping plate 312 to be absorbed by gold absorber layer 231. Layer 231 is preferably deposited upon the lower surface of plate 312. The sample 15 is similar to other samples described above and is connected to piezoelectric transducer 16. Bonding agent 14 is applied as usual.

Figure 10:
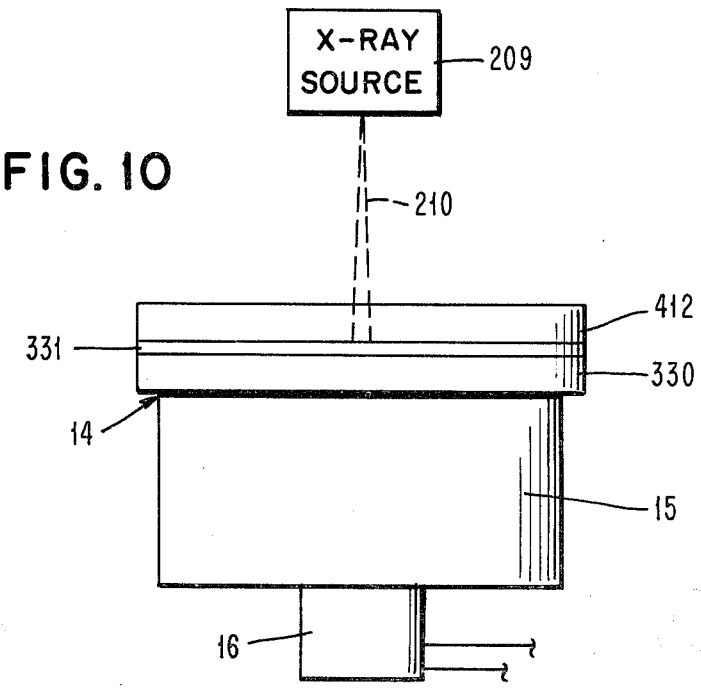
FIG. 10 shows an X-ray-to-acoustic-energy converter.

FIG. 10 shows a pulsed X-ray source 209 directing an X-ray beam 210 through a clamping layer 412 of perylene preferably, which is 10–100μ thick deposited upon a film 331 about 200Å thick composed of Fe. Film 331 is deposited upon glass plate 330 bonded by agent 14 to sample 15. A sensor 16 is included. The source of X-rays 209 uses pulsed X-rays from a material having a higher Z (atomic number) than absorber layer 331. Thus, the X-rays may be Kα X-rays emanating from a copper target when absorber layer 331 is composed of iron which has a lower Z than copper.

Note that energy could be directed through sample 15 in FIG. 1A, etc. instead of the clamping medium 12 if sample 15 is transparent to the energy.

What is claimed is:

1. Transducer apparatus for generating acoustic waves in response to application of a source of energy thereto comprising:
   a body of a solid material adapted for acoustic vibration,
   an energy absorbing layer composed of a thin film of solid opaque metallic material for absorbing energy,
   a bonding agent located between said body and said absorbing layer for maintaining said body in intimate acoustic contact with said body of solid material,
   a solid clamping medium,
   said absorbing layer being disposed intermediate said body and said clamping medium, and
   said medium being a substrate for said energy absorbing layer so said medium is in intimate acoustic contact with said absorbing layer for acoustically clamping said absorbing layer together with said body whereby acoustic vibration occurs in said body in response to said energy.

2. Transducer apparatus for generating acoustic waves in response to application of a source of energy thereto comprising:
   a body of a solid material adapted for acoustic vibration,
   an energy absorbing layer composed of a thin film of solid opaque metallic material for absorbing energy in intimate acoustic contact with said body of solid material,
   a solid clamping medium,
   said absorbing layer being disposed intermediate said body and said clamping medium,
   said medium being in intimate acoustic contact with said absorbing layer for acoustically clamping said absorbing layer together with said body whereby acoustic vibration occurs in said body in response to said energy, and
   said body being adapted for transmitting said energy and said medium comprises polished quartz and said absorbing layer is composed of molybdenum.

3. Transducer apparatus for generating acoustic waves in response to application of a source of energy thereto comprising:
   a body of a solid material adapted for acoustic vibrations,
   an energy absorbing layer composed of a thin film of solid opaque metallic material for absorbing energy in intimate acoustic contact with said body of solid material,
   a solid clamping medium,
   said absorbing layer being disposed intermediate said body and said clamping medium,
   said medium being in intimate acoustic contact with said absorbing layer for acoustically clamping said absorbing layer together with said body whereby acoustic vibration occurs in said body in response to said energy,
   said clamping medium comprising a substrate for said energy absorbing layer, and
   said layer and said body being juxtaposed in acoustically bonded relationship by a film of propylene glycol.

4. Transducer apparatus in accordance with claim 1 wherein said source of energy is directed towards said clamping medium through means for focusing said energy upon a specific point upon said energy absorbing layer.

5. Transducer apparatus in accordance with claim 4 wherein said point upon which said energy is focused is varied in size.

6. Transducer apparatus for generating acoustic waves in response to application of a source of energy thereto comprising:
   a body of a solid material adapted for acoustic vibration,
   an energy absorbing layer composed of a thin film of solid opaque metallic material for absorbing energy in intimate acoustic contact with said body of solid material,
   a solid clamping medium,
   said absorbing layer being disposed intermediate said body and said clamping medium,
   said medium being in intimate acoustic contact with said absorbing layer for acoustically clamping said absorbing layer together with said body whereby acoustic vibration occurs in said body in response to said energy,
   said source of energy being directed towards said clamping medium through means for focusing said energy upon a specific point upon said energy absorbing layer, and
   said point upon which said energy is focused is moved transversely relative to said energy absorbing layer whereby the location of vibration in said body is scanned across said body for searching said 7. Transducer apparatus in accordance with claim 6 including sensor means coupled to said body for detecting vibration applied thereto as a function of motion of said point across said layer.

8. Transducer apparatus for generating acoustic waves in response to application of a source of energy thereto comprising:
   a body of a solid material adapted for acoustic vibration,
   an energy absorbing layer composed of a thin film of solid opaque metallic material for absorbing energy,
   a bonding agent located between said body and said absorbing layer for maintaining said body in intimate acoustic contact with said body of solid material,
   a solid clamping medium,
   said absorbing layer being disposed intermediate said body and said clamping medium, said medium being a substrate for said energy absorbing layer so said medium is in intimate acoustic contact with said absorbing layer for acoustically clamping said absorbing layer together with said body whereby acoustic vibration occurs in said body in response to said energy, said energy absorbing layer comprising a thin film electrical resistor having a pair of electrical contacts adapted for connection to a source of a pulse of electrical energy.

9. Transducer apparatus in accordance with claim 1 wherein said energy absorbing layer comprises a thin film of a material highly absorbent of electromagnetic radiation adapted to be exposed thereto through said clamping medium, and said clamping medium having a high conductance of said electromagnetic radiation.

10. Transducer apparatus in accordance with claim 1 wherein said source of energy comprises electromagnetic radiation and said body is adapted for transmission of electromagnetic energy.

11. Transducer apparatus in accordance with claim 10 wherein said source of electromagnetic radiation comprises a source of heat.

12. Transducer apparatus in accordance with claim 10 wherein said source of electromagnetic radiation comprises X-ray.

13. Transducer apparatus in accordance with claim 10 wherein said source of electromagnetic radiation comprises a laser.

14. Transducer apparatus in accordance with claim 1 wherein said source of energy comprises an atomic source, and said body is highly conductive of energy from said atomic source.

15. Transducer apparatus in accordance with claim 14 wherein said atomic source comprises an ion beam.

16. Transducer apparatus for generating acoustic waves comprising:
a substrate of aluminum oxide,
a layer of tungsten deposited upon said substrate,
a block of solid material, and
said layer and a conforming surface of said block being juxtaposed in acoustically bonded relationship by a film of propylene glycol.

17. Transducer apparatus for generating acoustic waves in response to application of energy thereto comprising:
a source of pulses of energy,
a body of material adapted for acoustic vibration having a surface with a thin film of solid opaque metallic material deposited thereon adapted to be exposed to said source of energy,
said surface with a thin film being highly absorptive of said energy, and
a solid clamping medium,
a bonding agent located between said surface with a thin film and said clamping medium for maintaining said medium in intimate acoustical contact with said surface with a thin film,
and said medium and said bonding agent having a characteristic of readily transmitting said energy from said source to said surface with a thin film.

* * * * *